United States Patent [19]

Sim

[11] Patent Number: 5,773,415
[45] Date of Patent: Jun. 30, 1998

[54] USE OF DES-ASPARTATE-ANGIOTENSIN I AS AN ANTI-CARDIAC HYPERTROPHIC AGENT

[75] Inventor: Meng Kwoon Sim, Singapore, Singapore

[73] Assignee: National University of Singapore, Singapore

[21] Appl. No.: 776,026

[22] PCT Filed: May 22, 1996

[86] PCT No.: PCT/SG96/00004

§ 371 Date: May 19, 1997

§ 102(e) Date: May 19, 1997

[87] PCT Pub. No.: WO96/37213

PCT Pub. Date: Nov. 28, 1996

[30] Foreign Application Priority Data

May 25, 1995 [SG] Singapore .......................... 9500519-5

[51] Int. Cl.[6] .................................... A61K 38/00
[52] U.S. Cl. ................................................ 514/15
[58] Field of Search ................................. 514/15

[56] References Cited

U.S. PATENT DOCUMENTS 5,231,083   7/1993   Linz et al. ................. 514/19

OTHER PUBLICATIONS

Blair–West et al, Journal of Clinical Endocrinology and Metabolism, 32:575–578 (1971).

Tsai et al, Journal of Medicinal Chemistry, vol. 18, No. 12, pp. 1180–1183 (1975).

Campbell et al, Endocrinology, vol. 100, No. 1, pp. 46–51 (1977).

Sim, Biochemical Pharmacology, vol. 45, No. 7, pp. 1524–1527 (1993).

Sim et al, Blood Pressure, 3:260–264 (1994).

Sim et al, Biochemical Pharmacology, vol. 48, No. 5, pp. 1043–1046 (1994).

Sim et al, European Journal of Pharmacology, 257:R1–R3 (1994).

Sim et al, European Journal of Pharmacology, vol. 278, pp. 175–178 (1995).

del Rio et al., "des–Asp–Angiotensin I: Its Identification in Rat Blood and Confirmation as a Substrate for Converting Enzyme", *Endocrinology*, vol. 108, No. 2, 1981, pp. 406–412.

*Primary Examiner*—Jerome D. Goldberg
*Attorney, Agent, or Firm*—Birch, Stewart, Kolasch & Birch, LLP

[57] ABSTRACT

The use of des-Aspartate-angiotensin I (Arg-Val-Tyr-Ile-His-Pro-Phe-His-Leu) as an anti-cardiac hypertrophic agent is described. The compound, given either intravenously or orally, prevented the development of experimentally-induced cardiac hypertrophy in rats. Its action was dose-dependent and the maximum anti-cardiac hypertrophic effect was obtained at a dose of(i) 180 ng/day when given intravenously, and (ii) 285 µg/day when given orally.

6 Claims, No Drawings

5,773,415

USE OF DES-ASPARTATE-ANGIOTENSIN I AS AN ANTI-CARDIAC HYPERTROPHIC AGENT

TECHNICAL FIELD

This invention relates to an anti-cardiac hypertrophic agent.

BACKGROUND ART

The interest in des-Aspartate-angiotensin I, a nine amino acid angiotensin peptide (Arg-Val-Tyr-Ile-His-Pro-Phe-His-Leu), as a peptide of the renin-angiotensin system was first generated when Blair-West and colleagues (Blair-West et al, *J. Clin Endocrinol. Metab.*, 32:575–578 (1971)) postulated a biosynthetic pathway for the production of angiotensin III by enzymatic $NH_2$-terminal degradation of angiotensin I to the nonapeptide and sequential action of angiotensin converting enzyme on this nonapeptide to produce the heptapeptide. Since then des-Aspartate-angiotensin I has been shown to be an excellent substrate of plasma and pulmonary angiotensin converting enzyme (Tsai et al, *J. Med Chem.*, 18:1 180–1183 (1975)) and that its pressor and steroidogenic actions are dependent on its conversion to angiotensin III (Campbell et al, *Endocrinology*, 100:46–50 (1977)). Recently we found that homogenates of rat aorta and hypothalamus degrade exogenous angiotensin I to mainly des-Aspartate-angiotensin I instead of angiotensin II and the enzyme responsible for the degradation was a specific aminopeptidase that was not inhibited by amastatin, bestatin and EDTA (Sim, *Blochem. Pharmacol.*, 45:1524–1527 (1993); Sim et al, *Blood Pressure*, 3:260–264 (1994) and Sim et al, *Biochem. Pharmacol.*, 48:1043–1046 (1994)). Des-Aspartate-angiotensin I has also been shown to attenuate the pressor action of angiotensin II and angiotensin III in the brain (Sim and Radhakrishnan, *Eur. J Pharmacol.*, 257:R1–R3 (1994)). Peripheally, it is able to potentiate the contractile action of angiotensin II on the rabbit aortic ring but to attenuate the contractile action of angiotensin III in the same tissue (Sim and Yuan, *Eur. J Pharmacol.*, 287:175–178 (1995)). These recent findings of ours seem to indicate that des-Aspartate angiotensin I is a functional peptide that may have undefined specific actions in ensuring the normal functioning of the cardiovascular system.

DISCLOSURE OF INVENTION

In the course of studying the cardiovascular pharmacology of des-Aspartate-angiotensin I, the nonapeptide has been found to attenuate significantly the experimentally-induced cardiac hypertrophy in rat. It has been surprisingly discovered that des-Aspartate-angiotensin I is effective in accordance with the present invention at an exceeding low dose, i.e. an i.v. dose of 180 ng (given over a period of 4 hours) per day for four days attenuates significantly the experimentally-induced cardiac hypertrophy in rats. Another significant finding is that, despite being a peptide des-Aspartate-angiotensin I is equally effective in attenuating the cardiac hypertrophy when given orally at 285 mg per day for four days. These findings show that des-Aspartate-angiotensin I is a highly specific anti-cardiac hypertrophic agent and is effective at concentrations that produce minimum or no secondary effects.

Therefore, the present invention is directed to the use of des-Aspartate-angiotensin I as an anti-cardiac hypertrophic agent or in the preparation of an anti-cardiac agent, for either the prevention or treatment of cardiac hypertrophy or a pharmaceutical composition for preventing or treating cardiac hypertrophy comprising an effective amount of des-Aspartate-angiotensin I and a pharmaceutically acceptable carrier or diluent or a method for preventing or treating cardiac hypertrophy, which comprises administering to a subject in need of treatment an effective amount of des-Aspartate-angiotensin I or a packaged pharmaceutical composition for preventing or treating cardiac hypertrophy comprising a container suitable for storing a pharmaceutical preparation, an effective amount of des-Aspartate-angiotensin I in said container, and instructions associated with said container giving instructions for hie use of said des-Aspartate-angiotensin I for preventing or treating cardiac hypertrophy.

MODES FOR CARRYING OUT THE INVENTION

In the practice of the method of the present invention, an effective amount of des-Aspartate-angiotensin I or a derivative or salt thereof, or a pharmaceutical composition containing the same, as described below, is administered to a subject, such as a human patient, via any of the usual and acceptable methods known in the art, either singly or in combination with other pharmaceutical agents such as captopril or other angiotensin converting enzyme inhibitors. The compound or composition can thus be administered orally, by suppository, or parenterally (e.g., intramuscularly, intravenously, subcutaneously or intradermally), and in the form of either solid or liquid dosage including tablets, suspensions, or solutions, as is discussed in more detail below. The administration can be conducted in single dosage form with continuous therapy or in single dose therapy ad libitum.

Useful pharmaceutical carries for the preparation of the pharmaceutical compositions hereof can be solids, liquids or mixtures thereof thus, the compositions can take the form of tablets, pills, capes, powders, enterically coated or other protected formulations, sustained release formulations, erodible formulations, implantable devices or components thereof, microsphere formulations, solutions, suspensions, elixirs, aerosols, and the like.

Water, saline, aqueous dextrose, and glycols are preferred liquid carriers, particularly (when isotonic) for injectable solution. The carrier can be selected from various oils including those of petroleum, animal, vegetable or synthetic origin, for example, peanut oil, soybean oil, mineral oil sesame oil, and the like. Suitable pharmaceutical excipients include starch, cellulose, talc, glucose, lactose, sucrose, gelatin malt, rice, flour, chalk, silica gel, magnesium stearate, sodium stearate, glycerol monostearate, sodium chloride, dried skin milk, glycerol, propylene glycol, water, ethanol, and the like. The compositions way be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, "Remington's Pharmaceutical Sciences", 15th Edt; Mwk Publishing Co., Easton (1975); see, e.g., pp. 1405–1412 and pp. 1461–1487. Such compositions will, in general contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the stage of the disease or condition, the severity thereof, the schedule of administration the age and physical characteristics of the subject, and so forth. Proper dosages may be established using clinical approaches familiar to the medicinal arts.

Although the initial work was conducted in a rat experimental model, it is expected that the invention can be utilized in various mammals including, but not limited to, mice, rabbits and humans.

EXAMPLE

Sources of Materials

Des-Aspartate-angiotensin I was obtained from Bachem (βubendorf. Switzerland). Des-Aspartate-angiotensin I can be prepared by techniques well known in the art. Adult Sprague Dawley rats (250–300 g) were obtained from the Animal Centre, National University of Singapore.

Induction of Cardiac Hypertrophy

The abdominal aorta of each animal was co-arcted to the size of a 23-gauge hypodermic needle with a silk thread according to the method described by Everett et al (*Hypertension*, 23:587–592 (1994)). Briefly, each animal was anesthetized with phenobarbital (5 mg/100 g, i.p.). An incision was made in the ventral abdominal wall to access the suprarenal portion of the abdominal aorta. This portion of the abdominal aorta was dissected free and a blunt 23-gauge needle was placed adjacent to the aorta. A ligature was placed around the blunt needle and the aorta The blunt needle was then removed, leaving the aorta constricted to the size of the needle. The resulting coarctation resisted the normal flow of blood from the heart to the lower portion of the body and placed an extra load on the heart. This extra load is believed to cause hypertrophy of the heart, especially the left ventricle.

Administration of Des-Aspartate-Angiotensin

Following the operation, each animal was administered one of the various doses of des-Aspartate-angiotensin I (dissolved in saline) per day for four days. The nonapeptide was administered either intravenously via a femoral vein catheter which was implanted during the co-arctation operation or orally via a 1 ml syringe with a blunt needle. The intravenous administration was carried out using a micro-injector which delivered 10 µl of the peptide solution per hour for four hours. For oral administration, the peptide was dissolved in 0.5 ml saline. Control animals with co-arcted abdominal aorta were administered saline instead of the peptide solution. Sham animals were animals that underwent the same surgical operations but their aortae were not co-arcted.

Determination of Cardiac Hypertrophy

On the fourth day following the co-arctation of the abdominal aorta, the animal was again anaesthetized with pentobarbital and the carotid and femoral blood pressure were determined via a carotid artery catheter and a femoral artery catheters respectively. Each catheter was connected to a Gould Statham (P23 ID) pressure transducer. The transducers were in turn connected to a MacLab Quad Bridge Amplifier coupled to a MacLab/8 Virtual Instrument System which displayed the mean arterial blood pressure in mm Hg. The difference in the two readings indicated the extent of co-arctation. The heart of each animal was then excised and the weight of the ventricles was determined. The index of the ventricle weight (in mg) over the body weight of the animal (in g) was taken as the index of hypertrophy. For sham-operated animals the index was around 2.5, for aorta-co-arcted animals the index was above 3.7.

Results

. The results of the study are summarized in Table 1. Des-Aspartate-angiotensin I has been found to be an effective agent in preventing the development of experimentally-induced cardiac hypertrophy. The anti-hypertrophic action is dose-dependent and its maximum action is brought about by an i.v. dose of 180 ng/day for four days or an oral dose of 285 µg/day for four days.

TABLE 1

Effects of des-Aspartate-angiotensin I on cardiac hypertrophy in rats

| Dose | | Hypertrophy Index[1] | CBP (mm Hg) | FBP (mm Hg) | BP (mm Hg) |
|---|---|---|---|---|---|
| No Administration | | | | | |
| Sham animals | | 2.53 ± 0.06 | 129 ± 13 | 129 ± 13 | 0 |
| Intravenous Administration | | | | | |
| Control animals | | 3.77 ± 0.06 | 151 ± 19 | 107 ± 22 | 44 |
| 23 ng | (19 pmol) | 3.72 ± 0.18 | 158 ± 17 | 106 ± 13 | 52 |
| 45 ng | (38 pmol) | *3.51 ± 0.09 | 159 ± 25 | 119 ± 18 | 40 |
| 90 ng | (76 pmol) | *3.47 ± 0.13 | 156 ± 15 | 124 ± 14 | 32 |
| 180 ng | (152 pmol) | *3.17 ± 0.14 | 142 ± 22 | 111 ± 25 | 31 |
| Oral Administration | | | | | |
| Control animals | | 3.75 ± 0.06 | 159 ± 18 | 110 ± 20 | 49 |
| 64 µg | (63.5 nmol) | *3.40 ± 0.10 | 153 ± 10 | 89 ± 27 | 64 |
| 128 µg | (125 nmol) | *3.23 ± 0.12 | 163 ± 27 | 121 ± 30 | 42 |
| 285 µg | (250 nmol) | *2.93 ± 0.09 | 171 ± 24 | 119 ± 33 | 52 |
| 590 µg | (500 nmol) | *3.13 ± 0.22 | 153 ± 22 | 110 ± 19 | 43 |
| 1180 µg | (1000 nmol) | *3.34 ± 0.16 | 154 ± 29 | 107 ± 25 | 46 |
| 1770 µg | (1500 nmol) | 3.57 ± 0.17 | 165 ± 14 | 123 ± 28 | 42 |

Each value is a means ± SEM obtained from 6 individual animals. Sham animals were animals that underwent the surgical operation but not the co-arctation of the abdominal aorta. Control animals were animals that underwent coarctation of the abdominal aorta but were given saline instead of the peptide solution.
[1]Hypertrophy Index = ventricle weight in mg/body weight in g.
CBP = mean arterial blood pressure obtained from the carotid artery catheter,
FBP = mean arterial blood pressure obtained from the femoral artery catheter,
BP = CBP − FBP.
*Significantly different from the control ($p < 0.05$, Student's t-test).

INDUSTRIAL APPLICABILITY

The industrial applicability of the invention is primarily in the medical or health care industry as an anti-cardiac hypertrophic agent in either the prevention or treatment of cardiac hypertrophy.

I claim:

1. A method of treating cardiac hypertrophy, which comprises administering to a subject in need thereof an effective amount of des-Aspartate-angiotensin I.

2. The method according to claim 1, wherein said des-Aspartate-angiotensin I is administered orally.

3. The method according to claim 1, wherein said des-Aspartate-angiotensin I is administered by suppository.

4. The method according to claim 1, wherein said des-Aspartate-angiotensin I is administered parenterally.

5. The method according to claim 1, wherein said des-Aspartate-angiotensin I is administered in the form of a solid dosage.

6. The method according to claim 1, wherein said des-Aspartate-angiotensin I is administered in the form of a liquid dosage.

* * * * *